United States Patent
Cottrell et al.

(10) Patent No.: US 9,000,240 B2
(45) Date of Patent: *Apr. 7, 2015

(54) INTEGRATED PROCESS FOR THE PRODUCTION OF 1-CHLORO-3,3,3-TRIFLUOROPROPENE

(75) Inventors: Stephen A. Cottrell, Williamsville, NY (US); Hsueh Sung Tung, Getzville, NY (US); Konstantin A. Pokrovski, Orchard Park, NY (US)

(73) Assignee: Honeywell International Inc., Morristown, NJ (US)

( * ) Notice: Subject to any disclaimer, the term of this patent is extended or adjusted under 35 U.S.C. 154(b) by 91 days.

This patent is subject to a terminal disclaimer.

(21) Appl. No.: 13/471,565

(22) Filed: May 15, 2012

(65) Prior Publication Data

US 2012/0296127 A1    Nov. 22, 2012

Related U.S. Application Data

(60) Provisional application No. 61/487,735, filed on May 19, 2011.

(51) Int. Cl.
| | | |
|---|---|---|
| *C07C 17/25* | (2006.01) | |
| *C07C 17/20* | (2006.01) | |
| *C07C 21/18* | (2006.01) | |
| *C07C 17/38* | (2006.01) | |
| *C07C 17/383* | (2006.01) | |

(52) U.S. Cl.
CPC ............... *C07C 21/18* (2013.01); *C07C 17/25* (2013.01); *C07C 17/383* (2013.01)

(58) Field of Classification Search
None
See application file for complete search history.

(56) References Cited

U.S. PATENT DOCUMENTS

| | | | |
|---|---|---|---|
| 6,235,951 B1 | 5/2001 | Sakyu et al. | |
| 6,329,559 B1 * | 12/2001 | Sievert et al. | 570/165 |
| 6,362,382 B1 * | 3/2002 | Chen et al. | 570/164 |
| 6,362,383 B1 | 3/2002 | Wilmet et al. | |
| 6,844,475 B1 * | 1/2005 | Tung et al. | 570/168 |
| 2009/0287027 A1 | 11/2009 | Merkel et al. | |
| 2010/0191025 A1 | 7/2010 | Perdrieux | |
| 2011/0105807 A1 | 5/2011 | Kopkalli et al. | |
| 2011/0201853 A1 | 8/2011 | Tung et al. | |
| 2011/0218370 A1 * | 9/2011 | Elsheikh et al. | 570/236 |
| 2012/0172636 A1 * | 7/2012 | Pokrovski et al. | 570/135 |

FOREIGN PATENT DOCUMENTS

| | | |
|---|---|---|
| WO | 2004106271 A2 | 12/2004 |
| WO | 2010059496 A1 | 5/2010 |
| WO | 2010088196 A2 | 8/2010 |
| WO | 2010111067 A1 | 9/2010 |
| WO | WO 2010111067 A1 * | 9/2010 |
| WO | 2011135416 A1 | 11/2011 |
| WO | 2012030797 A2 | 3/2012 |

OTHER PUBLICATIONS

Wikipedia (tetramethylene sulfone).*
PCT ISR & Written Opinion issued in PCT/US2012/038269 dated Jan. 21, 2013.
EP Supplementary Search Report issued in EP12786229.0 dated Sep. 29, 2014.

* cited by examiner

*Primary Examiner* — Fereydoun G Sajjadi
*Assistant Examiner* — Medhanit Bahta
(74) *Attorney, Agent, or Firm* — Bruce O. Bradford

(57) ABSTRACT

The present invention is directed to processes for the production of 1233zd from 240fa and HF, with or without a catalyst, at a commercial scale. The 240fa and HF are fed to a reactor operating at high pressure. The resulting product stream comprising 1233zd, HCl, HF, and other byproducts is treated to one or more purification techniques including phase separation and one or more distillations to provide purified 1233zd, which meets commercial product specifications, i.e., having a GC purity of 99.5% or greater.

10 Claims, No Drawings

INTEGRATED PROCESS FOR THE PRODUCTION OF 1-CHLORO-3,3,3-TRIFLUOROPROPENE

CROSS-REFERENCE TO RELATED APPLICATION

This application claims domestic priority to commonly owned, U.S. Provisional Patent Application Ser. No. 61/487,735, filed May 19, 2011, the disclosure of which is hereby incorporated herein by reference.

BACKGROUND OF THE INVENTION

This invention related to the production of 1-chloro-3,3,3-trifluoropropene (1233zd) on a commercial scale from the reaction of 1,1,1,3,3-pentachloropropane (240fa) and HF. The compound 1233zd is a low global warming compound that has applications as a replacement for high global warming materials, for example in foam blowing and aerosol propellant applications.

The designation 1233 is used herein to refer to all trifluoro, monochloro propenes, namely olefin compounds having the general formula $C_3H_2ClF_3$. The designation 1233zd is used herein generically to refer to 1,1,1-trifluo-3,chloro-propene, independent of whether it is the cis form or the trans form. The terms "cis-1233zd" and "trans-1233zd" are used herein to describe the cis- and trans-forms of 1,1,1-trifluo-3-chlororo-propene, respectively. The designation "1233zd" therefore includes within its scope cis-1233zd, trans-1233zd, and all combinations and mixtures of these.

U.S. Pat. No. 6,844,475 teaches a process for producing 1233zd from 240fa at low pressure and at temperatures lower than 150° C. The disclosure of this patent is hereby incorporated herein by reference.

U.S. Pat. No. 6,362,383 teaches a process for preparing 1,1,1,3,3-pentafluoropropane (245fa) by (1) a first reaction step in which 1,1,1,3,3-pentachloropropane (240fa) is reacted with hydrogen fluoride in the liquid phase in the presence of a first hydrofluorination catalyst under conditions that are suitable for obtaining a mixture of reaction products comprising 1-chloro-3,3,3-trifluoropropene (1233zd) in substantial amount, and (2) a second reaction step in which the 1-chloro-3,3,3-trifluoropropene (1233zd) obtained from the first step is reacted with hydrogen fluoride in the liquid phase in the presence of a second hydrofluorination catalyst, and preferably while hydrogen chloride is continuously fed in, in order to obtain 1,1,1,3,3-pentafluoropropane (245fa). The disclosure of this patent is hereby incorporated herein by reference.

SUMMARY OF THE INVENTION

The present invention is directed to processes for the production of 1233zd from 240fa and HF, with or without a catalyst, at a commercial scale. The 240fa and HF are fed to a reactor operating at high pressure. The resulting product stream comprising 1233zd, HCl, HF, and other byproducts is treated to a series of purification techniques including phase separation and one or more distillations to provide purified 1233zd, which meets commercial product specifications.

In one embodiment of the process, 240fa and HF are fed to a reactor operating at high pressure (i.e., from 150 psig to 600 psig);

(a) the resulting product stream comprising 1233zd, HCl, HF, and other byproducts are distilled and the bottoms product, rich in HF, is recycled to the reactor;

(b) the overhead product from the distillation column is fed to a second distillation column to remove the HCl;

(c) the HCl in the overhead stream is scrubbed with water and recovered as an aqueous solution;

(d) the bottom stream from the second distillation column is then phase separated to recover HF;

(e) the HF rich top layer of the phase separation is recycled back to the reactor; and (f) the phase separation bottom layer components including the desired 1233zd are scrubbed, dried and distilled to meet commercial product specifications.

In another embodiment of the process, 240fa and HF are fed to a reactor operating at high pressure. The resulting product stream comprising 1233zd, HCl, HF, and other byproducts is partially condensed to recover HF by phase separation. The recovered HF phase is recycled to the reactor. The HCl is scrubbed from the vapor stream and recovered as an aqueous solution. The remaining organic components including the desired 1233zd are scrubbed, dried and distilled to meet commercial product specifications.

The main difference between these two embodiments is that it has been discovered that the HF and organic do not easily phase separate if the HCl is still present, which is an unexpected result. Accordingly, in the preferred embodiment, the HCl is removed first.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

In one embodiment of the process, 240fa and HF are fed to a reactor operating at high pressure. The resulting product stream comprising 1233zd, HCl, HF, and other byproducts are distilled and the bottoms product, rich in HF, is recycled to the reactor. The overhead product from the distillation column is fed to another distillation column to remove HCl. The HCl in the overhead stream is scrubbed with water and recovered as an aqueous solution. The bottom stream from distillation column is phase separated to recover HF. The HF rich top layer of the phase separation is recycled back to the reactor. The phase separation bottom layer components including the desired 1233zd are scrubbed, dried and distilled to meet commercial product specifications.

As described above, one embodiment of the present invention provides a process for the production of 1233zd from 240fa and HF, with or without a catalyst, at a commercial scale. The details of this process are as follows:

(1) High pressure liquid phase reaction of 240 and HF, with or without a catalyst, forming 1233zd, its byproducts, HCl and unreacted HF;

(2) First distillation of the stream from step (1) and recycle of the bottoms to the reactor of step (1);

(3) Second distillation of the overhead stream of step (2);

(4) Separation and recovery of the HCl rich overhead stream of step (3) as an aqueous solution in water;
(5) Phase separation of the bottoms stream of step (3) to form an HF rich layer and an organic rich layer, with recycle of the HF rich layer to the reactor of step (1);
(6) The organic rich layer from step (5) is fed to a caustic scrubber to remove any remaining acidity and dried with an appropriate drying agent such as sulfuric acid or molecular sieves; and
(7) The acid-free, dry stream from step (6) is distilled to produce 1233zd meeting all product specifications.

If desired, the process steps may be modified such that HF is removed in step (5), for example, by using absorption in sulfuric acid.

As described above, the high pressure liquid phase reaction of 240 and HF, with or without a catalyst, yields a product stream comprising 1233zd, byproducts, HCl and unreacted HF. In certain embodiments the pressure range is from 150 psig to 600 psig. In certain embodiments, a more preferred pressure range is from 230 psig to 500 psig and a most preferred pressure range is from 350 psig to 450 psig.

In certain embodiments, the catalyst choices are selected from known Lewis acid catalysts. The preferred catalysts are $TiCl_4$ or $SbCl_5$, with $TiCl_4$ being more preferred. In certain embodiments, the most preferred choice is operation of the reactor without employing any catalyst.

The typical byproducts observed in the reaction stream are precursors to 1233zd such as 241fa, 242fa, and 243fa. These can easily be separated from the reaction stream using known techniques and recycled.

The HCl recovery step entails the feeding of the organic layer from the second distillation to an HCl recovery system to remove and recover HCl as a solution in water. In certain embodiments, the HCl is recovered using a packed-bed scrubber and falling-film absorber to form a high-strength solution that may be sold or used as a raw material for other processes, such as the production of calcium chloride. Optionally, the HCl may be distilled in a simple distillation column using a low-temperature cooling medium ($-40°$ C. to $-100°$ C.) to obtain a stream that is essentially-free of HF, which may be more desirable as a commercially saleable product.

In certain embodiments, the phase separation takes place in a vessel appropriate to allow for separation of the organic and HF phases such as a simple horizontal tank. The phase separation takes place at a similar temperature and pressure as the condensation of the previous step. As described above, this step can also include the recycle of the HF-rich layer back to the reactor in step (1). In certain embodiments, the HF-layer is collected in a vessel and fed continuously back to the reactor of step (1).

As described above, in this step the HCl-free organic components are distilled to remove recyclable intermediates to 1233zd. In certain embodiments the materials distilled are higher-boiling precursors to 1233zd such as 241fa and 242fa. These materials may be present in ranges of 1% to 20% of the crude 1233zd stream.

In step (6), the overhead stream from step (5) is fed to a caustic scrubber to remove any remaining acidity and dried with an appropriate drying agent such as sulfuric acid or molecular sieves. In certain embodiments, the drying agents that are appropriate may be selected from known materials such as: 3A to 5A molecular sieves, high strength sulfuric acid, calcium sulfate and silica gels. In certain embodiments, the caustic scrubber consists of a packed-tower with a circulating solution of NaOH or KOH.

In step (7) the acid-free, dry stream from Step (6) is distilled to produce 1233zd, meeting all commercial product specifications. In certain embodiments, commercial product specifications include a GC purity of 99.5% or greater, with low levels, e.g., less than 100 ppm, of unsaturated compounds.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the manufacture of 1233zd comprising the steps of:
   (a) reacting 240fa and HF in the liquid phase and in the absence of a catalyst in a reactor operating at high pressure to produce a product stream comprising 1233zd, HCl, HF, and other byproducts;
   (b) distilling the product stream from step (a) into a first overhead product and a first bottoms product rich in HF;
   (c) distilling the first overhead product from step (b) to form a second overhead product containing HCl and a second bottoms product containing organic components and HF;
   (d) phase separating the second bottoms product from step (c) to separate the HF from the organic components; and
   (e) caustic scrubbing, drying, and distilling the organic components from step (d) to provide purified 1233zd;
   wherein the reactor pressure range is from 150 psig to 600 psig; and
   wherein the compound 1233zd, produced in step (e) has a purity of 99.5% or greater, as measured using gas chromatography.

2. The process of claim 1, wherein the reactor pressure range is from 230 psig to 500 psig.

3. The process of claim 1, wherein the reactor pressure range is from 350 psig to 450 psig.

4. The process of claim 1, wherein the HF from step (b) is recycled to the reactor.

5. The process of claim 1, wherein the HCl from step (c) is scrubbed with water and optionally recovered as an aqueous solution.

6. The process of claim 1, wherein the HF from the phase separation in step (d) is recycled back to the reactor.

7. The process of claim 1, wherein the caustic scrubbing is conducted with NaOH or KOH.

8. The process of claim 1, wherein the drying agent in step (e) comprises sulfuric acid.

9. The process of claim 1, wherein the drying agent in step (e) comprises molecular sieves.

10. A process for making highly purified HCFC-1233zd by the reaction of 240fa and HF at a reactor pressure of from 150 psig to 600 psig wherein the purification of the HCFC-1233zd comprises the steps of:
(a) distilling the resulting product stream comprising HCFC-1233zd, HCl, HF, and other byproducts;
(b) distilling the overhead product from the step (a) distillation in a second distillation column to remove the HCl;
(c) phase separating the bottom stream from the second distillation in step (b) to isolate the HF; and
(d) purifying the phase separation bottom layer components from step (c) to yield purified HCFC-1233zd having a purity of 99.5% or greater, as measured using gas chromatography.

* * * * *